United States Patent [19]
Grove

[11] Patent Number: 5,257,770
[45] Date of Patent: Nov. 2, 1993

[54] CONTROL OF FLUID FLOW

[76] Inventor: Dale Grove, 72 Buckingham Dr., Billerica, Mass. 01821

[21] Appl. No.: 872,403

[22] Filed: Apr. 23, 1992

[51] Int. Cl.$^5$ ................................. F16K 7/04
[52] U.S. Cl. ................................. 251/4; 251/297
[58] Field of Search ................... 251/4, 247, 6

[56] References Cited

U.S. PATENT DOCUMENTS 1,330,523  2/1920  Evitts et al. ................... 251/6
3,099,429  7/1963  Broman ...................... 251/297 X
4,337,791  7/1982  Tech et al. .................. 251/297 X Primary Examiner—John C. Fox
Attorney, Agent, or Firm—George E. Kersey

[57] ABSTRACT

Precision control of fluid flow by a body containing an inclined surface opposite an elongated opening, with a slider inserted into the opening to be movable along the opening in contact with discrete portions of the body which desirably includes a hinged detent for making contact with the body.

19 Claims, 9 Drawing Sheets

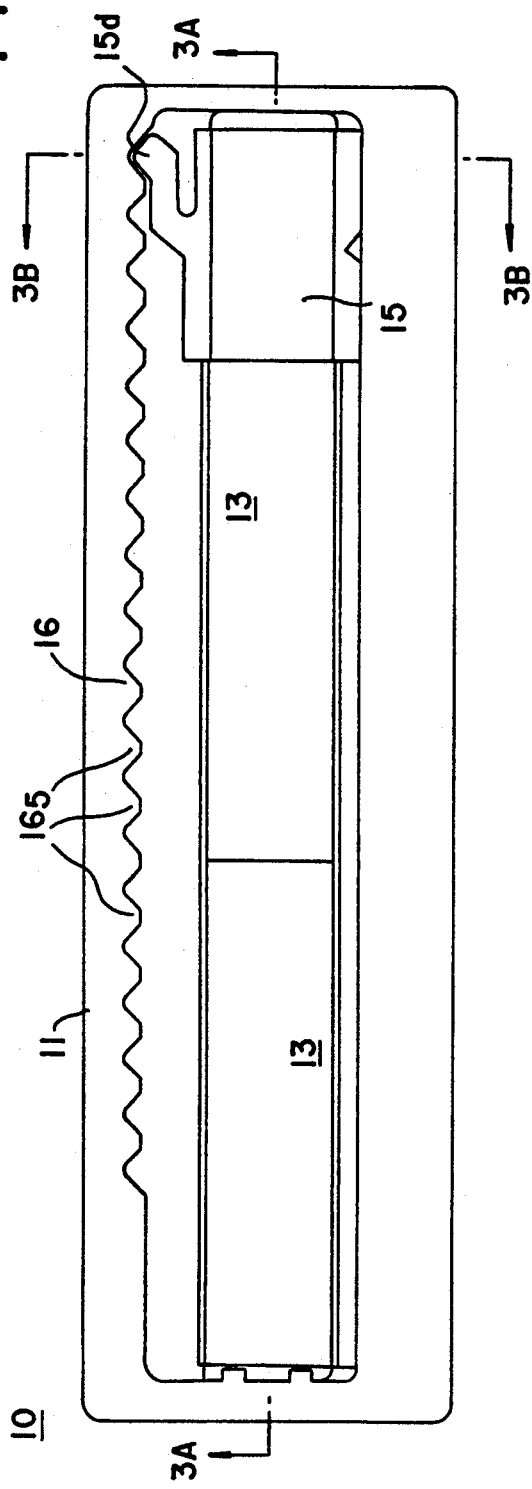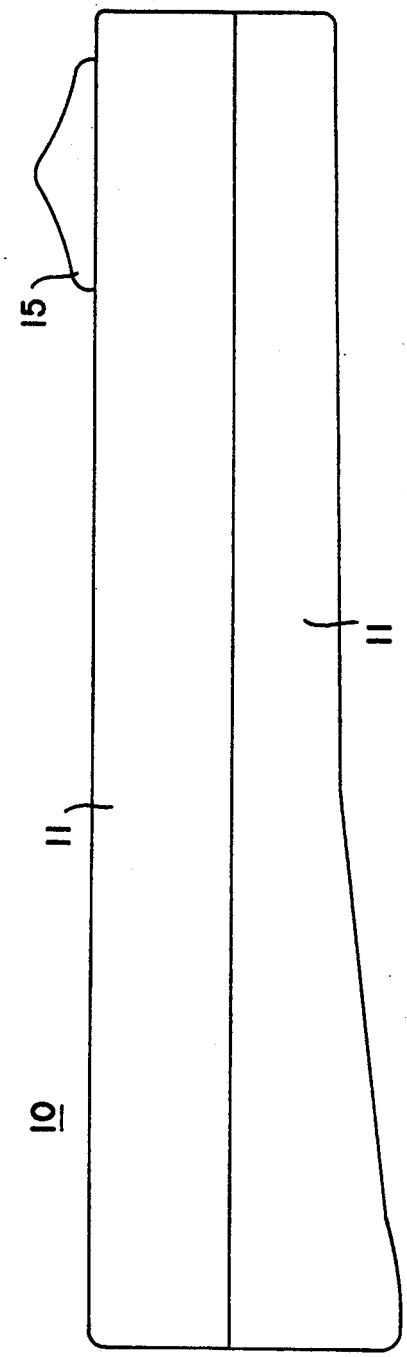

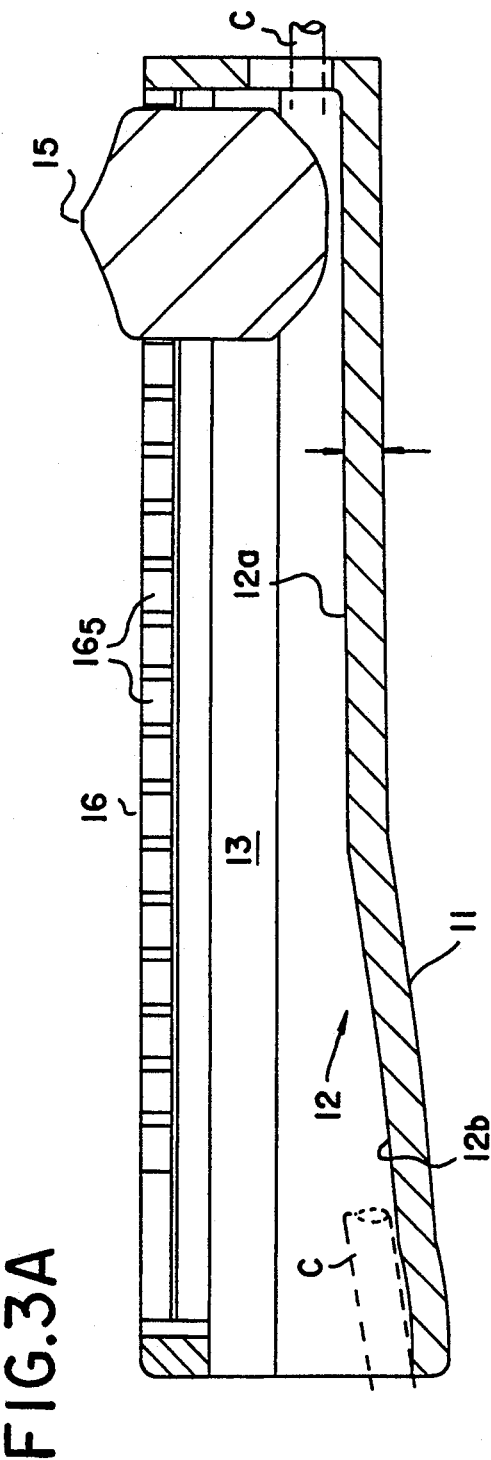
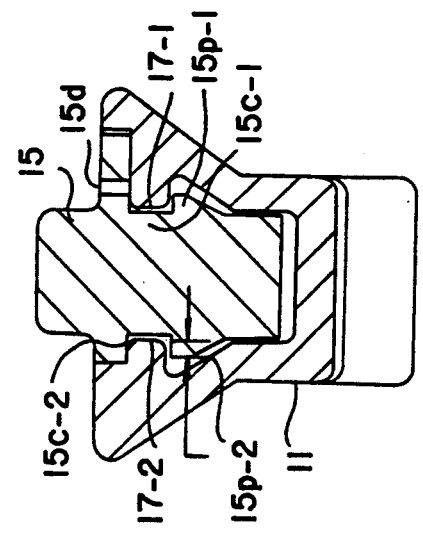
FIG.3A
FIG.3B

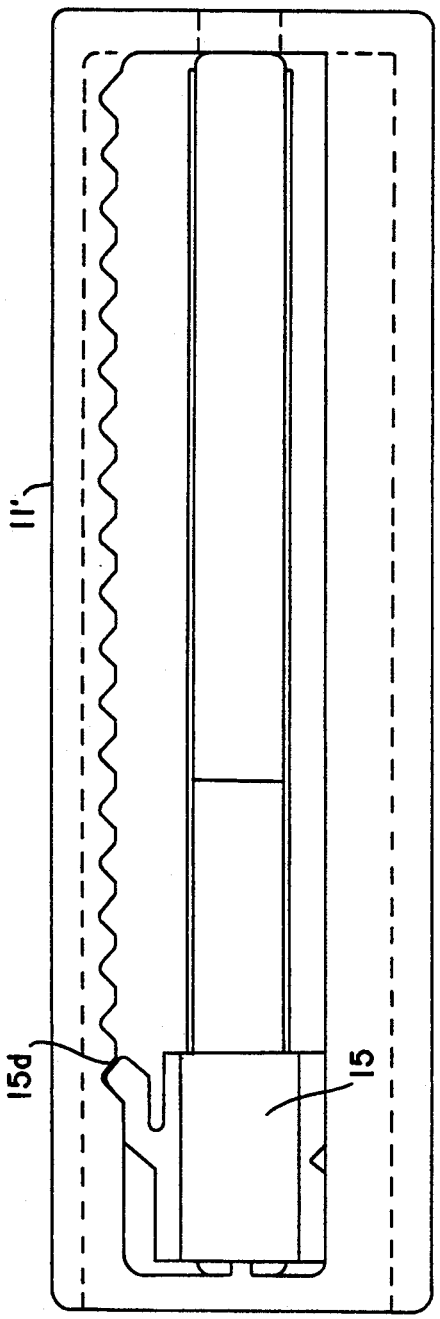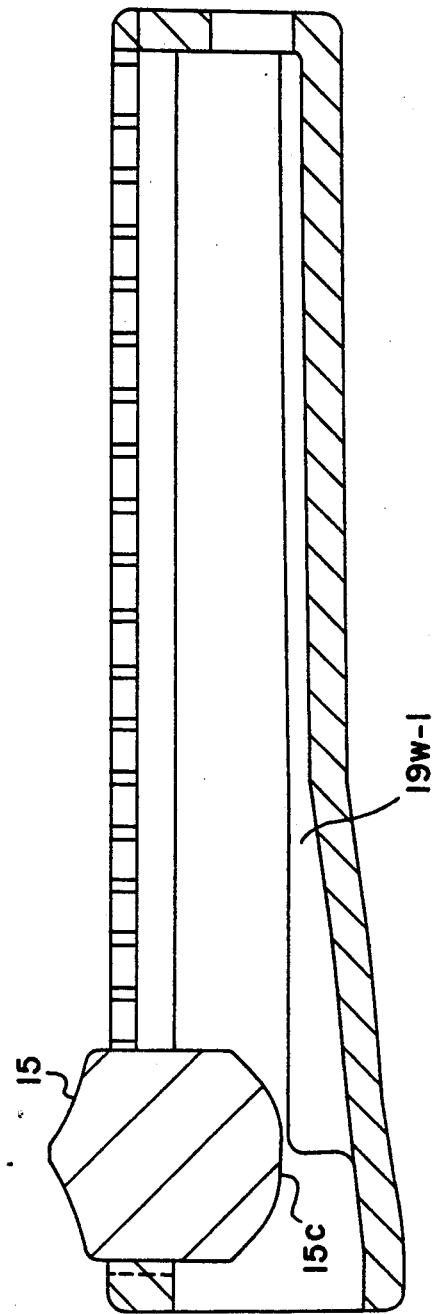
FIG.6
FIG.7

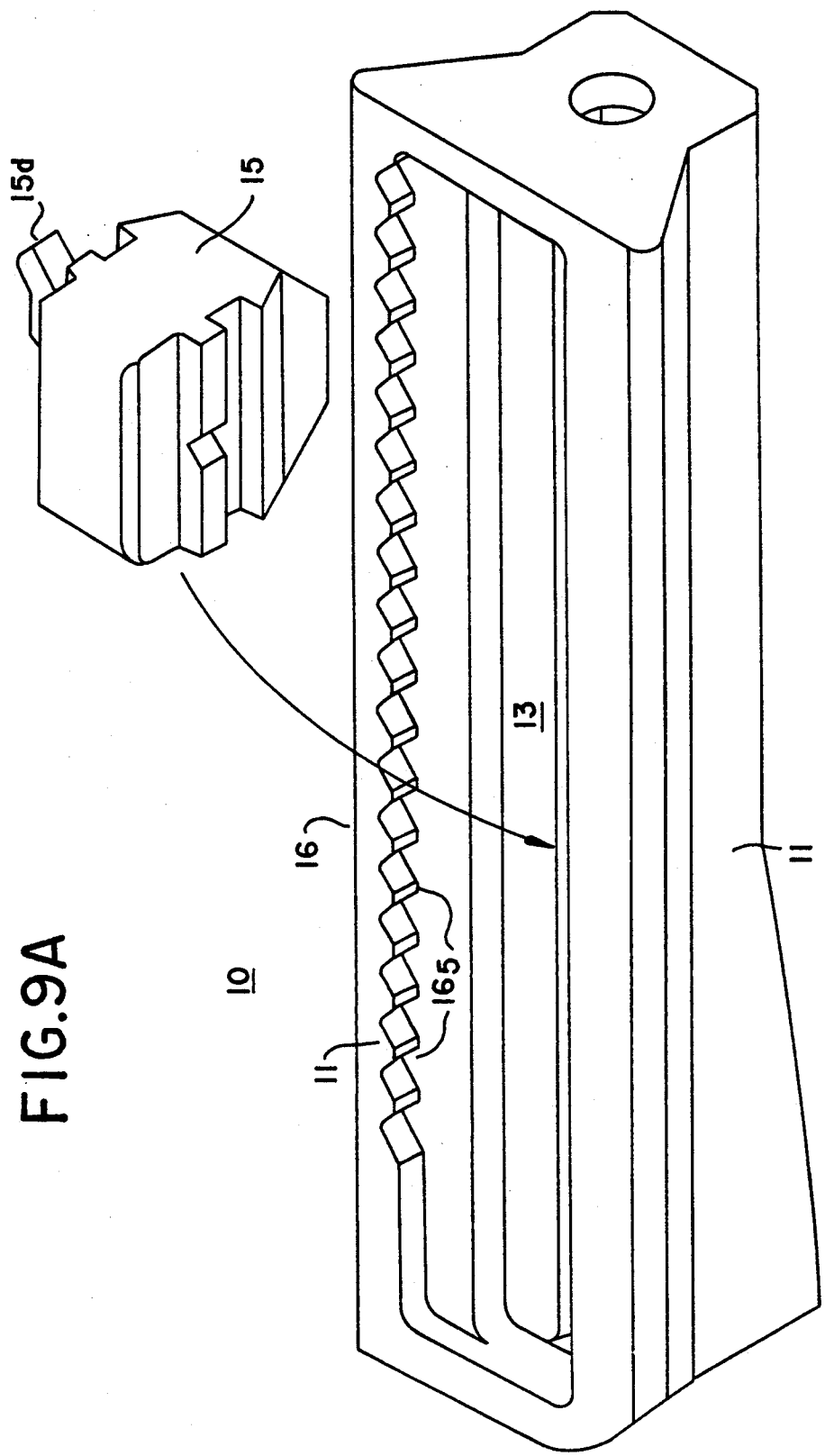

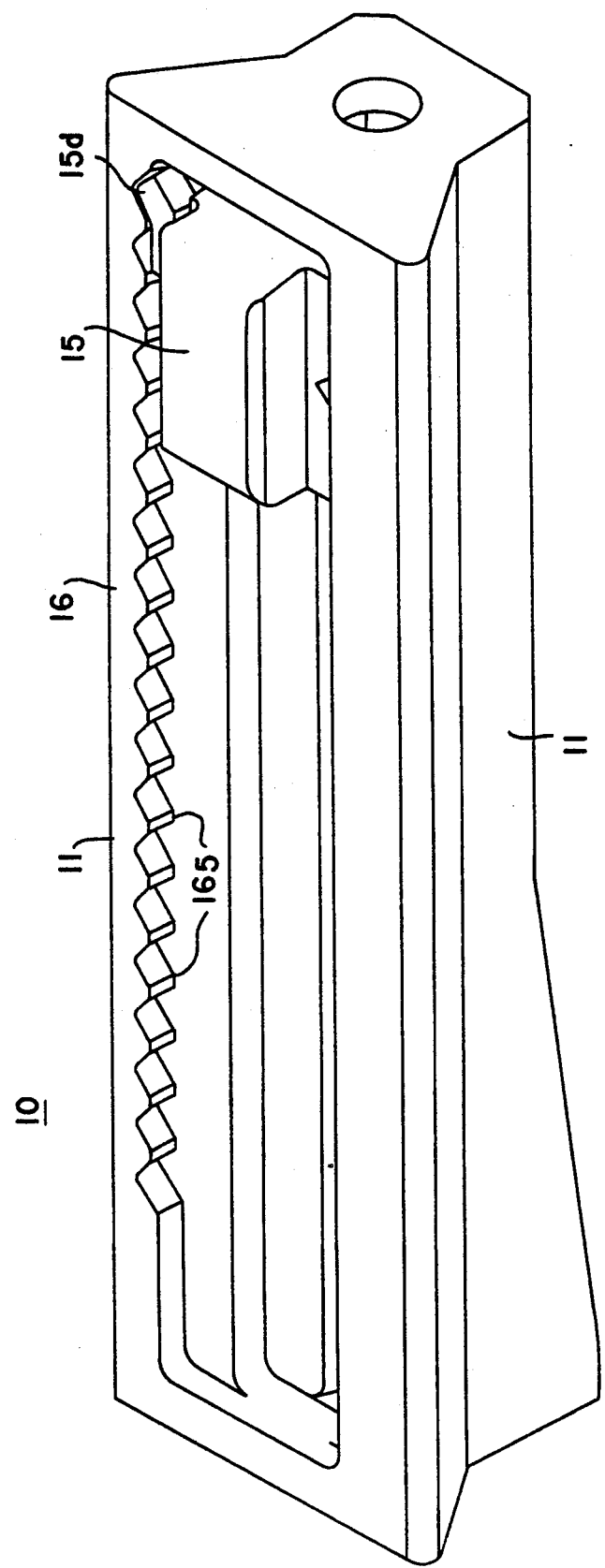

CONTROL OF FLUID FLOW

BACKGROUND OF THE INVENTION

This invention relates to the precision control of the flow of fluids through flexible conduits and, more particularly, to the control of fluid flow through tubing used in biomedical application.

In biomedical practice the flow of therapeutic and other fluids to a patient is controlled using various clamps which typically have an "on" and "off" position.

Since biomedical fluids are usually applied through plastic tubing, the clamps often hold their positions with difficulty. This is because the compression of a plastic tube to terminate flow produces stress within the tubing and because of the naturally low coefficient of friction associated with plastic materials.

Even in cases where attempts have been made to guard against inadvertent movement of the flow control device, the techniques that have been employed generally rely upon a ratchet with a rotatable member such that inadvertent force on the tubing, for example when a patient moves, can dislodge and alter the flow control setting of the device.

Illustrative examples of the prior art include: Tersteegen U.S. Pat. No. 4,429,852 "Adapter"; Stephens U.S. Pat. No. 4,193,174 "Lever and Fulcrum Clamping Assembly"; McGrath U.S. Pat. No. 4,380,103 "Balloon Clip"; MacNeil U.S. Pat. No. 4,346,869 "Tube Clamp".

Other illustrative examples of the prior art are set forth in the tabulation below:

| U.S. Pat. No. & (Issue Date) | Patentee & (Title) | Assignee |
|---|---|---|
| 4,911,399 (3/27/90) | Green (Cam Valve for Regulation of Fluid Flow Through Flexible Tubing) | Anglo-American, Inc. |
| 4,337,791 (7/6/82) | Tech et al (Flow Control Regulator) | La-Van Tech Development Corp. |
| 4,335,866 (6/22/82) | Bujan (Flow Control Device) | Abbott Laboratories |
| 4,247,076 (1/27/81) | Larkin (Toggle Action Tubing Clamp) | Abbott Laboratories |
| 3,984,081 (10/5/76) | Hoganson (Medical Device for Controlling Flow of Intravenous Solutions) | The Raymond Lee Organization, Inc. |
| 3,960,149 (6/1/76) | Bujan (Flow Control Device) | Abbott Laboratories |
| 3,847,370 (11/12/74) | Engelscher (Tubing Servicing Device) | Horizon Industries Ltd. |
| 3,802,463 (4/9/74) | Dabney (Flow Control Apparatus) | Cutter Laboratories, Inc. |
| 3,612,474 (10/12/71) | Strohl, Jr. (Flow Control Device for Flexible Tubes) | Abbott Laboratories |
| 3,329,391 (7/4/67) | Deane (Surgical Pinch Valve) | |
| 3,215,395 (11/2/65) | Gorbar (Regulating Clamp for Flexible Tubes) | |
| 3,135,259 (6/2/64) | Evans (Infusion Flow Control Valve) | Sterilon Corp., |
| 3,099,429 (7/30/63) | Broman (Roller Clamp for Parenteral Solution Equipment) | Baxter Laboratories, Inc. |
| 2,595,511 (5/6/52) | Butler (Pinch Valve) | |
| 1,330,523 (10/20) | Evitts et al (Tube Clamp) | | that applies counterforce to the closing element. In some cases the counterforce is sufficient to open a clamp that has been set into a closed position.

In addition, the application of pinching forces to plastic tubing tends to produce distortion and flattening of the tubing. This not only can interfere with the flow of fluid, the clamp positions can create weaknesses and subsequent failure in the tubing.

Another difficulty with conventional flow control clamps is that they are imprecise in adjustment. Not only is it difficult to arrive at a setting for a prescribed flow rate, once a desired setting is attained, it is difficult to hold because of the counterpressure applied as a result of the compressive force applied to the tubing, Although a number of clamping devices with serrations for positioning a clamp against a flexible tube are in the prior art, none of these provide the security against inadvertent movement of the tubing with respect to its housing as needed in modern biomedical procedures.

Accordingly, it is an object of the invention to promote the control over the flow of fluids through conduits, particularly for biomedical applications. A related object is to enhance the amount of control that can be exercised in the case of flow through plastic tubing.

Another object of the invention is to achieve precision control over the amount of fluid flow and permit accurate adjustment over the amount of fluid flow and permit accurate adjustment over the amount of flow. A related object is to achieve this kind of precision in the case of biomedical fluids applied through plastic tubing.

SUMMARY OF THE INVENTION

In accomplishing the foregoing and related objects the invention provides for the precision control of fluid flow by a body containing an inclined surface opposite an elongated opening, with a slider inserted into the opening to be movable along the opening in contact with discrete portions of the body which desirably includes a hinged detent for making contact with the body.

In accordance with one aspect of the invention the body includes a serrated edge for making contact with the detent. In addition, the inclined surface of the body can include a plurality of regions having different degrees of declination. The serrations of the edge can form a saw-tooth with uniformly distributed teeth for making contact with the detent. The teeth of the saw-tooth desirably have flattened crests and bases.

In accordance with another aspect of the invention, an edge of the body opposite the saw-tooth is callibrated in accordance with the control over flow through the body determined by the position of the slider within the elongated opening. A conduit within the body can extend through the body opposite the elongated opening. The conduit desirably is a plastic tube inserted through the body below the elongated opening.

In a method for the precision control of fluid flow, the steps include providing a body containing an inclined surface opposite an elongated opening, and inserting, into the opening, a slider which is movable along the opening in contact with discrete portions of the body. The slider is moved incrementally along the opening to control fluid flow through the body. The method also can include the step of inserting a conduit through the body in the direction of elongation of the opening, and bringing the slider into contact with the conduit to control the throughflow of fluid.

The conduit can be a plastic tube, with the slider flattening the tube during movement along the opening in order to control the flow of fluid. The slider can have an initial region of travel along the opening where the tube is flattened without changing the cross-section of flow.

In a method of fabricating apparatus for the precision control of fluid flow the steps can include molding a body containing an inclined surface opposite an elongated opening and separately molding a slider which is insertable into the opening to be movable along the opening in contact with discrete portions of the body.

The body can be molded with internal tracks for receiving the slider, which is, in turn molded with channels for engaging the tracks, so that the slider is inserted into the opening with the channels of said slider in engagement with the tracks of the body. The slider is then movable along the opening in contact with discrete portions of the body. The slider can be molded with protuberances that respectively bound the channels, and the slider inserted into the body with the protuberances pushed beyond the tracks.

The slider can be inserted into the body at an intermediate position along the length of the opening to facilitate the insertion of the slider into contact with the tracks of the body by the outward displacement of the walls of the body during insertion of the slider.

The body can be molded with discrete inclined surfaces having different degrees of declination, and the body can have opposed ends, one of which is provided with an opening of reduced cross-section to receive a conduit, with the opposite end open and surrounded by the walls of the body.

BRIEF DESCRIPTION OF THE DRAWINGS

Other aspects of the invention will become apparent after considering several illustrative embodiments taken in conjunction with drawings in which FIG. 1 is a top view of a flow control device in accordance with the invention;

FIG. 2 is a side view of the flow control device of FIG. 1;

FIG. 3A is a sectional view of the flow control device of FIG. 1 taken along the lines 3A—3A;

FIG. 3B is a sectional view of the device of FIG. 1 taken along the lines 3B—3B;

FIGS. 6 and 7 are respective top and side views of an alternative flow control device in accordance with the invention;

FIGS. 9A through 9C are perspective views corresponding to FIGS. 1–5D.

DETAILED DESCRIPTION

Figure 4B:
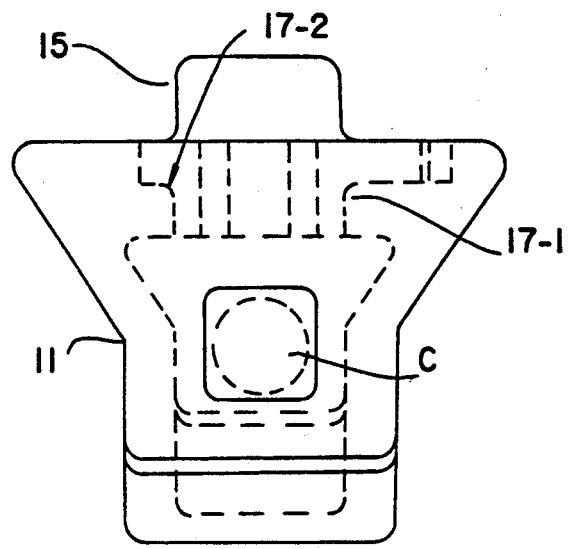
FIG. 4B is an inlet end view of the device of FIGS. 1 and 2.

With reference to the drawings, a flow control device 10 in accordance with the invention for the precision control of fluid flow shown in FIGS. 1, 2 and 3A includes a body 11 containing an inclined surface 12 (FIG. 3A) opposite an elongated opening 13, with a slider 15 inserted into the opening 13 to be movable therealong in contact with discrete upper portions of the body 11 as shown in FIGS. 1 and 3A. The slider 15 desirably includes a hinged detent 15d for making contact with the body 11.

Suitable contact between the slider 15 and the body 11 is by a serrated edge 16 engaged at discrete positions by the detent 15. In addition, the inclined surface 12 of the body 11 can include a plurality of regions 12a and 12b having different degrees of declination. The serrations 16s of the edge 16 can form a saw-tooth with uniformly distributed teeth for making contact with the detent 15d. The teeth 16s of the saw-tooth desirably have flattened crests and bases.

The edge 16 of the body 11 opposite the saw-teeth can be calibrated in accordance with the control over flow through the body 11 determined by the position of the slider 15 within the elongated opening 13. A conduit C within the body 11 can extend through the body 11 opposite the elongated opening 13. The conduit C desirably is a plastic tube inserted through the body 11 below the elongated opening 13.

In the precision control of fluid flow, a body is provided containing an inclined surface 12 opposite an elongated opening 13, and inserting, into the opening 13, a slider 15 which is movable along the opening 13 in contact with discrete portions 16s of the body 11. The slider 15 is moved incrementally along the opening 13 to control fluid flow through the body 11. A conduit C may be inserted through the body 11 in the direction of elongation of the opening 13, and bringing the slider 15 into contact with the conduit C to control the through-flow of fluid.

The conduit C can be a plastic tube, with the slider 15 flattening the tube during movement along the opening 13 in order to control the flow of fluid. The slider 15 can have an initial region 12a of travel along the opening 13 where the tube C is flattened without changing the cross-section of flow.

In fabricating apparatus for the precision control of fluid flow, a body 11 is molded containing an inclined surface 12 opposite an elongated opening 13. A slider 15 is separately molded and inserted into the opening 13 to be movable along the opening 13 in contact with discrete portions 16s of the body 11.

The body 11 can be molded with internal tracks 17-1 and 17-2 (FIG. 3B) for receiving the slider 15, which is, in turn molded with channels 15c-1 and 15c-2 (FIG. 3B) for engaging the tracks 17-1 and 17-2, so that the slider 15 is inserted into the opening 13 with the engagement members of the slider in engagement with the tracks of the body.

The slider 15 is then movable along the opening 13 in contact with discrete portions 16s of the body 11. The slider 15 also can be molded with protuberances 15p-1 and 15p-2 that respectively bound the channels 15c-1 and 15c-2. The slider 15 inserted into the body 11 with the protuberances 15p-1 and 15p-2 pushed beyond the tracks 17-1 and 17-2.

The slider 15 can be inserted into the body 11 at an intermediate position along the length of the opening 13 to facilitate the insertion of the slider 15 into contact with the tracks 17-1 and 17-2 of the body 11 by the outward displacement of the walls of the body 11 during insertion of the slider 15.

Figure 4A:
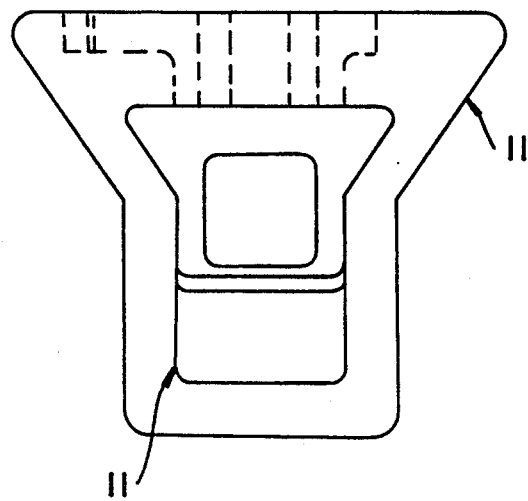
FIG. 4A is an outlet end view of the device of FIGS. 1 and 2.
Figure 5A:
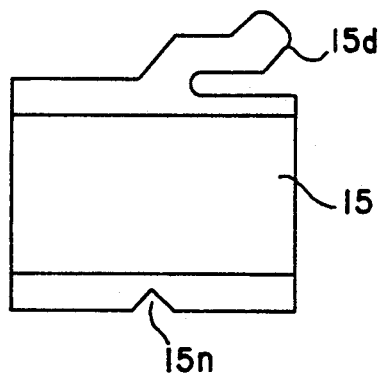
FIG. 5A is a top view of a slider with a contacting detent for the device of FIGS. 1 and 2.
Figure 5C:
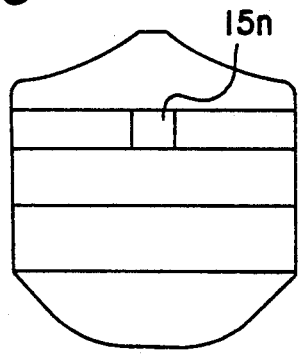
FIGS. 5B and 5C are respective front and side views of the slider of FIG. 5A.
Figure 5B:
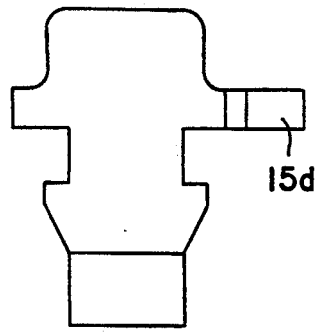
Figure 5D:
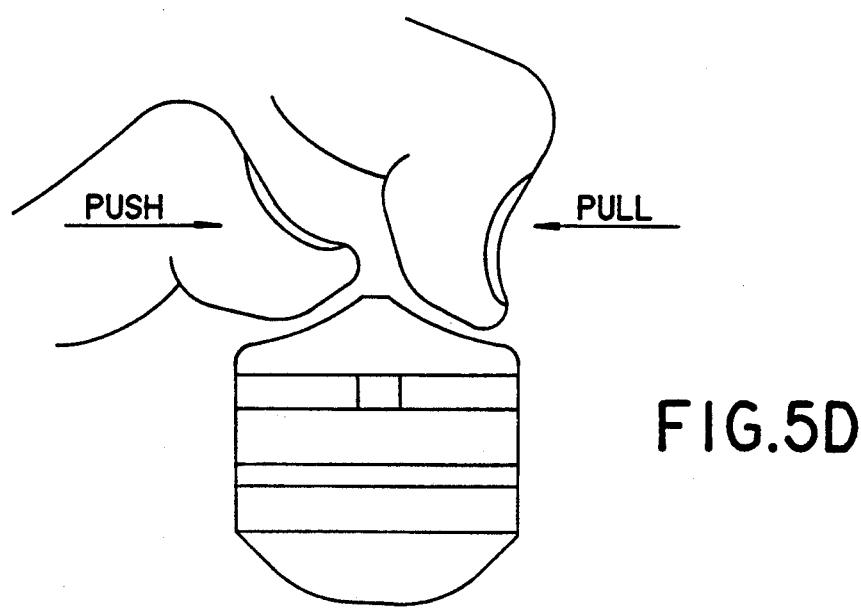
FIG. 5D is a further view of FIG. 5B showing the manipulation of the slider for the precision control of fluid flow.

The body 11 can be molded with discrete inclined surfaces 12a and 12b having different degrees of declination, and the body 11 can have opposed ends, one of which is provided with an opening of reduced cross-section as shown in FIG. 4B to receive a conduit C, with the opposite end shown in FIG. 4A open and surrounded by the walls of the body 11.

Figure 8B:
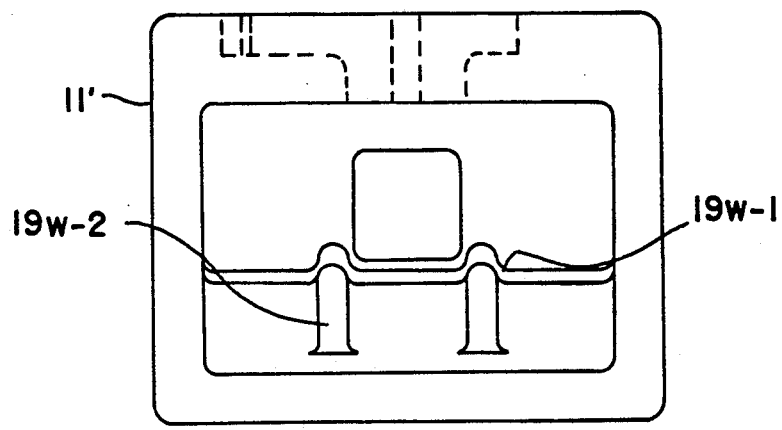
FIGS. 8A and 8B are respective outlet and inlet end views of the device of FIGS. 6 and 7.
Figure 8A:
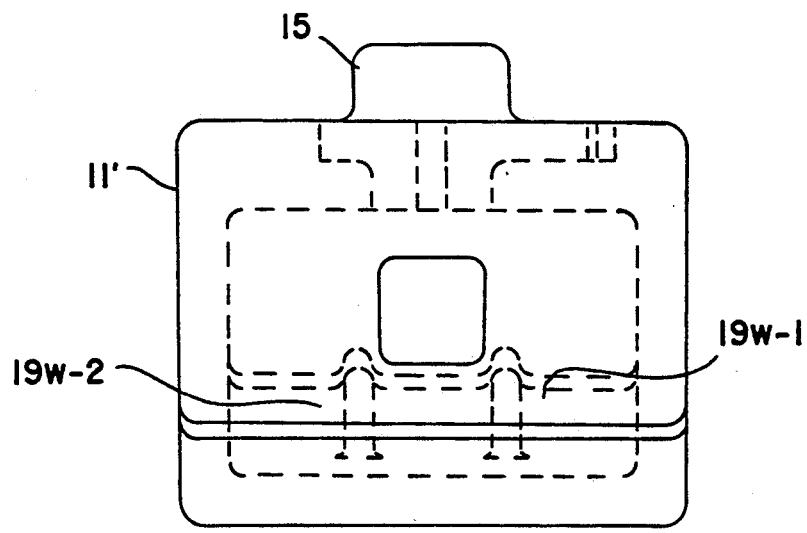

In the alternate embodiment of FIG. 6, which is a top view of a flow control device in accordance with the invention, the body 11' is provided with the same slider 15 used in FIG. 1, but the inlet and outlet ends have a rectangular cross-section as shown in FIGS. 8A and 8B.

In order to suitably position a conduit (not shown), the body 11' includes internal upstanding walls 19w-1 and 19w-2 which serve as a channel for the conduit and an initial guide channel for the lower portion of the slider 15c. In FIG. 7, which is a side view of the alternative flow control device of FIG. 6, only one of the upstanding walls 19w-1 is visible, but both walls 19w-1 and 19w-2, and their taper, are shown in FIG. 8A, which is an outlet end view of the device of FIGS. 6 and 7, and in FIG. 8B, which is an inlet end view of the device of FIGS. 6 and 7.

Figure 9C:
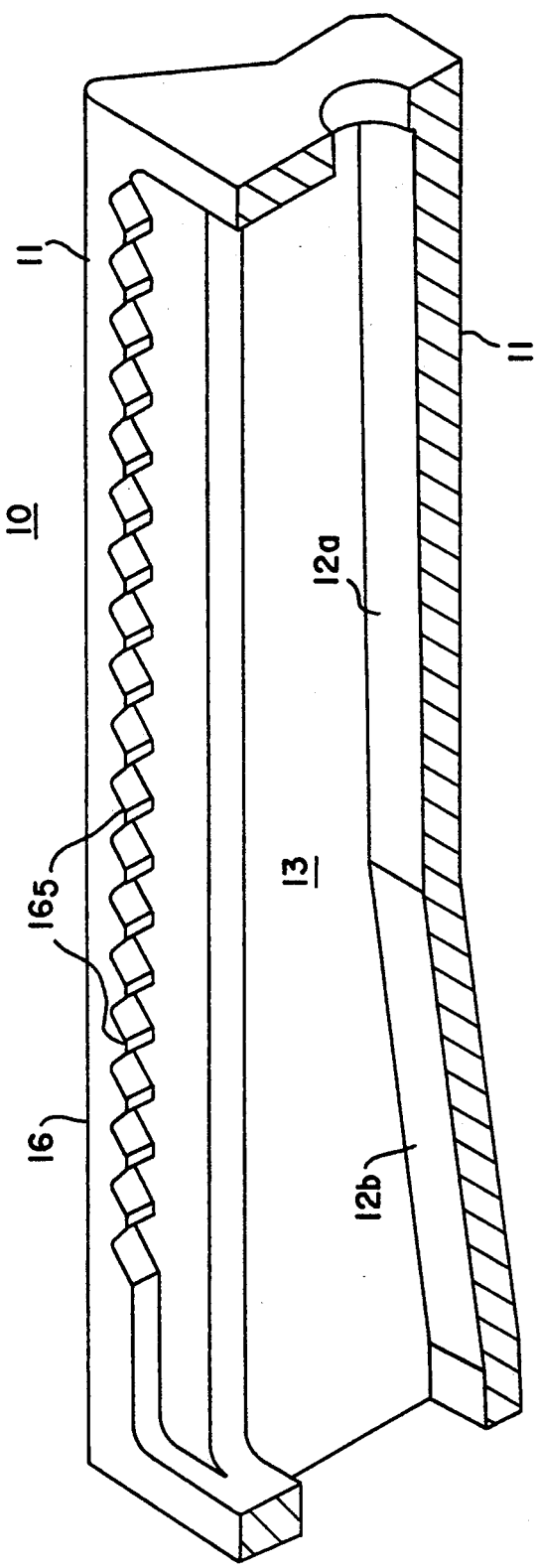

FIGS. 9A through 9C are perspective views corresponding to FIGS. 1-5D.

The foregoing detailed description is illustrative only and other implementations and adaptations of the invention will be readily apparent to those of ordinary skill in the art.

What is claimed:

1. Apparatus for the precision control of fluid flow in a conduit comprises
    a body containing an inclined surface opposite an elongated opening;
    means for permitting the conduit to extend through said body in the direction of elongation of said opening; and
    a slider inserted into said opening and movable therealong in contact with discrete portions of said body and said conduit;
    wherein said slider includes a hinged detent for making said contact with said body.

2. Apparatus as defined in claim 1 wherein said body includes serrations along an edge of said opening for making contact with said detent.

3. Apparatus as defined in claim 2 wherein said the serrations of said edge form a saw-tooth with uniformly distributed teeth for making contact with said detent.

4. Apparatus as defined in claim 3 wherein the teeth of said saw-tooth have flattened crests and bases.

5. Apparatus as defined in claim 4 wherein an edge of said body opposite said saw-tooth is calibrated in accordance with the control over flow through said body determined by the position of said slider within said elongated opening.

6. Apparatus as defined in claim 1 wherein said inclined surface includes a plurality of regions having different degrees of declination.

7. Apparatus as defined in claim 1 further including a conduit within said body extending therethrough opposite said elongated opening.

8. Apparatus as defined in claim 7 wherein said conduit is a plastic tube inserted through said body below said elongated opening.

9. A method for the precision control of fluid flow which comprises the steps of:
    (A) providing a body containing an inclined surface opposite an elongated opening;
    (B) inserting in said opening a slider which is movable along said opening in contact with discrete portions of said body and includes a hinged detent for making said contact with said body; and
    (C) extending a conduit through said body in the direction of elongation of said opening and contactable with said slider.

10. The method of claim 9 wherein said slider s moved incrementally along said opening to control fluid flow through said body.

11. The method of claim 10 including the step of inserting a conduit through said body in the direction of elongation of said opening and bringing said slider into contact with said conduit to control the flow of fluid therethrough.

12. The method of claim 11 wherein said conduit is a plastic tube and said slider flattens said tube during movement along said opening in order to control the flow of fluid therethrough.

13. The method of claim 12 wherein said slider has an initial region of travel along said opening where said tube is flattened without changing the cross-section of flow therethrough.

14. Apparatus which comprises:
    (A) a body containing an inclined surface opposite an elongated opening; and (B) a separately molded slider, including a hinged detent, which slider is insertable into said opening to be movable along said opening with said hinged detent in contact with discrete portions of said body.

15. The apparatus of claim 4 wherein said body has internal tracks for receiving said slider and said slider has channels for engaging said tracks, wherein said slider is inserted into said opening with the channels of said slider in engagement with the tracks of said body so that said slider is movable along said opening with said hinged detent in contact with discrete portions of said body.

16. The apparatus of claim 15 wherein said slider has protuberances that respectively bound said channels and said slider is inserted into said body with said protuberances pushed beyond said tracks.

17. The apparatus of claim 14 wherein said slider is inserted into said body at an intermediate position along the length of said opening to facilitate the insertion of said slider into contact with the tracks of said body by the outward displacement of the walls of said body during insertion of said slider.

18. The apparatus of claim 14 wherein said body has discrete inclined surfaces having different degrees of declination.

19. The apparatus of claim 14 wherein said body has opposed ends, one of which is provided with an opening of reduced cross-section to receive a conduit and the opposite end of which is open and surrounded by the walls of said body.

* * * * *